United States Patent
Roovers et al.

(10) Patent No.: US 6,184,313 B1
(45) Date of Patent: Feb. 6, 2001

(54) HYBRID SILANE DENDRIMER-STAR POLYMERS

(75) Inventors: Jacques Roovers, Gloucester; Bogdan Comanita, Ottawa, both of (CA)

(73) Assignee: National Research Council of Canada

(*) Notice: Under 35 U.S.C. 154(b), the term of this patent shall be extended for 0 days.

(21) Appl. No.: 09/349,108

(22) Filed: Jul. 8, 1999

(51) Int. Cl.$^7$ .................................................. C08F 283/00
(52) U.S. Cl. ............................ 525/474; 528/15; 528/31; 528/35; 424/16 DIG
(58) Field of Search ............................ 525/474; 528/15, 528/31, 35; 424/16 DIG

(56) References Cited

U.S. PATENT DOCUMENTS

| | | |
|---|---|---|
| 5,225,521 | 7/1993 | Spinu . |
| 5,275,838 | 1/1994 | Merrill . |
| 5,276,110 | * 1/1994 | Zhou et al. . |
| 5,648,186 | 7/1997 | Daroux et al. . |

FOREIGN PATENT DOCUMENTS

2076166 * 2/1994 (CA) .

OTHER PUBLICATIONS

Lorenz et al: Marcromolecules, vol. 28, pp. 6657–6661 <1995>.
Ponomarenko et al. in Mol. Cryst. Liq. Cryst. Sci. Technol., Sect. A (1999), 332, 2553 (abstract).*
Ponomarenko et al. in Vysokomol. Soedin. Ser. A, Ser. B (1998) 49(8), 1253 (abstract).*
Domanita et al. in Polym. Sci. Mat. Eng. (1998), 79, 271 (abstract).*

* cited by examiner

*Primary Examiner*—Robert Dawson
*Assistant Examiner*—Marc S. Zimmer
(74) *Attorney, Agent, or Firm*—J. Wayne Anderson

(57) ABSTRACT

A silane or carbosilane dendrimer is modified with bridge moieties and polymer arms attached to the bridges to form hybrid dendrimer-star polymers. The bridge moieties are attached via Si—C bonds to the silane or dendrimer. The bridge has one or more reactive groups to which polymer arms are attached. Selected reactive groups on the bridge may serve as initiator sites for in situ polymerization of the arms. The polymer arms are of the polyether, polysulfide or polyester type. These arms may have functional groups which allow further modification and attachments. For this type of star polymer, the bridge has been found to increase resistance to hydrolysis at the silane- or dendrimer-arm junction. These star polymers are useful e.g. as viscosity modifiers, component in molding resins, water solubilizer for hydrophobic molecules, surfactants and as carriers for drugs, prodrugs and other biological agents.

20 Claims, No Drawings

HYBRID SILANE DENDRIMER-STAR POLYMERS

FIELD OF THE INVENTION

This invention relates to silane and carbosilane dendrimers having bridge moieties at the periphery, and to star polymers formed by attaching arms to sites on the bridge. The arms are polymers formed in situ from monomers at initiator sites on the bridge, or preformed polymer attached at reactive sites on the bridge. The bridge may be selected alkyl, cycloalkyl, aryl, alkaryl, aralkyl, small polyether or small polysulfide groups. The arms may be polyethers, polysulfides or polyesters. Copolymers of these polymer types may be used.

BACKGROUND AND PRIOR ART

Recently polyethers of the type of poly(ethylene oxide) (PEO) and poly(ethylene glycol) (PEG) have found application in biological and pharmaceutical contexts because of properties including water solubility, biocompatibility e.g. non-thrombogenic, and terminal hydroxy groups to attach various entities including drugs, prodrugs and other biological agents.

These polyethers (PEO, PEG) have been used as outer arms in star polymers where the cores have been divinylbenzene (may be cross-linked), poly(ethylene imine), poly (amidoamines) and heptaphenyl. See for instance:

U.S. Pat. No. 5,275,838, Jan. 4,1994, Merrill; and

U.S. Pat. No. 5,648,186, Jul. 15, 1997, Daroux et al.

Polyester arms formed by ring-opening polymerization of lactones, lactides and glycolides have been used with cores of polyesters, sugar type molecules or inositol, to form star polymers. See for instance:

U.S. Pat. No. 5,225,521, Jul. 6, 1993, Spinu.

Carbosilane dendrimers have been used as cores in hybrid dendrimer-star polymers. These dendrimers provide a nonpolar and chemically inert scaffold that is advantageous when thermal and hydrolytic stability is required, and in hydrophobic environments. See for example:

U.S. Pat. No. 5,276,110, Jan. 4, 1994, Zhou et al.

When these carbosilane dendrimers, having peripheral silane termini, were used as cores with arms of poly (alkylene oxide), it was found that the core-arm interface was unduly susceptible to hydrolysis in some applications. It would be desirable to reconfigure this interface in order to reduce susceptibility to hydrolysis.

The periphery of carbosilane dendrimers having outer allyl silane groups, has been modified to introduce hydroxy groups by controlled oxidation. See Lorenz et al in: Macromolecules 28, 6657–6661 (1995). No outer arms of any type of polymer were incorporated in this reference.

We have studied modifying the outer surface of carbosilane dendrimers to reduce hydrolytic cleavage at the corearm interface when arms of polyalkylene oxide and the like are used in hybrid dendrimer-star polymers.

SUMMARY OF THE INVENTION

It has now been found that by inserting selected bridge molecules at the core-arm interface (when the core is silane or carbosilane and the arm is polyether, polysulfide or polyester) the susceptibility to hydrolysis is reduced significantly. In this context by hydrolysis is meant the breaking of chemical bonds at the dendrimer periphery and the release of functional groups or polymer chains from the dendrimerpolymer hybrid.

The invention includes a silane- or carbosilane-based, periphery-modified dendrimer, adapted to serve as core in hybrid dendrimer-star polymers, comprising:
  a) an inner structure having a central silane nucleus and, optionally, multiple carbosilane branches extending outwardly from the nucleus in a repetitive generational manner yielding silane termini;
  and, attached to the silane or silane termini by a hydrolysis-resistant bond;
  b) bridge moieties comprising groups selected from alkyl of at least 4 C atoms, cycloalkyl, aryl including aralkyl and alkaryl, and polyether and polysulfide of up to about 6 repeating units, the moieties having reactive groups enabling attachment of polymer arms thereto.

The invention also includes a hybrid dendrimer-star polymer, comprising:
  (i) the modified dendrimer described in the previous paragraph except that the alkyl bridge moiety has at least 2C atoms, and
  (ii) outer arms comprising polymer chains selected from polyethers, polysulfides, polyesters and copolymers thereof, the arms being attached to the dendrimer at the sites of the bridge reactive groups.

The invention further includes a process of preparing a hybrid dendrimer-star polymer including a modified silane or carbosilane dendrimer and selected polymer outer arms, comprising:
  a) attaching bridge moieties to reactive silane sites in a silane or carbosilane dendrimer, the bridge comprising a group selected from alkyl, cycloalkyl, aryl, aralkyl, alkaryl, small polyether and small polysulfide, the bridges having reactive groups thereon; and
  b) reacting a selected form of the bridge reactive groups with one of:
    (i) monomer selected from alkylene oxide, alkylene sulfide, alkylene glycol, alkylene dithiol, and hydroxyalkanoic acid and lactone thereof, under polymerization conditions, said selected form serving as initiator, to form polymer arm attached to the bridge; and
    (ii) functionalized prepolymer selected from polyether, polysulfide, polyester and copolymers thereof, to attach prepolymer to the bridge, thereby to form the star polymer.

A primary aspect of the invention may be defined as: in a star polymer having a silane or carbosilane core and outer arms comprising polymer selected from polyether, polysulfide, polyester and copolymers thereof, the improvement comprising selected bridge inserts positioned between the core and the arms, with the bridge attached to silicon atoms in the core or dendrimer by a Si—C bond, the length and type of the bridge and of the arm being selected to give desired properties e.g. hydrophilic/hydrophobic balance or solubility, to the polymer-dendrimer hybrid.

DETAILED DESCRIPTION

The silane or carbosilane core has a regular usually dendritic structure and is built up in stages or generations from a central silane or disilane nucleus e.g. by alternating hydrosilylation and vinylation or allylation reactions. Various dendritic carbosilanes are known and any would be operative provided that the bridges can be formed at the peripheral silane group. The core size can range from generation zero to generation 5 or even higher e.g. to 8. For generation zero, one or up to 5 silicon atoms can suffice.

The carbosilane dendrimers provide a non-polar and relatively inert scaffold that can be used under various reaction conditions including anionic polymerization conditions.

The bridge moiety is bonded to silane or to peripheral silane sites in the carbosilane dendrimer by a hydrolysis-resistant Si—C bond.

Preferably the bridge moiety is selected from (1) —R—X; where R is selected from alkyl and cycloalkyl having from 4 to 18 C atoms; aryl, aralkyl and alkaryl having from 6 to 18C atoms; and X is hydroxyl, thiol, amine, carboxyl, aldehyde, halide or a protecting group therefor;

and (2)

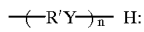

where R' is alkyl having from 2 to 4C atoms, Y is oxygen or sulfur and n is 2 to 6, and the bridge-core attachment comprises the hydrolysis-resistant bond Si—C.

Preferred bridge members include ($C_4$–$C_9$ alkyl)—Z, cyclohexyl, phenyl or benzyl or para-methylenephenyl)—Z, and

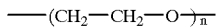

H where Z is a reactive group such as OH, —$NH_2$ or —COOH and n=2–6, as well as the corresponding thiols and thioethers. In the aryl, aralkyl and alkaryl bridge moieties the aryl may be phenyl or lower alkyl-substituted phenyl, naphthyl, biphenyl (may be alkyl-substituted) or pyridine, and the alkyl may be $C_1$ to $C_6$ straight chain or branched.

Where the bridge is cycloalkyl or aryl it is possible to have two reactive groups at selected locations on the ring or rings. This allows for doubling the number of arms and facilitates masking or isolation of the core, reduction of influence of core properties and/or increasing the number of modifiable functional groups.

Suitable protecting groups for the reactive groups on the bridge moiety are illustrated as follows:

| Reactive Group | Protecting Group |
| --- | --- |
| hydroxyl | tetrahydropyran, |
| thiol | (S) -benzyl |
| amino | 2,2,5,5-tetramethyl-1-aza-2,5-disilacyclopentane |
| carboxylic acid | 4,4'-dimethyl-2-oxazoline |
| aldehyde | acetal such as 1,3-dioxolane |

These are typical protecting groups; however many others are known and may be used.

Where the bridge moiety is a polyether or polysulfide it should be attached to the (peripheral) silane site by a Si—C bond and be of low molecular weight e.g. not more than 6 repeating units.

Any suitable process may be used to attach the bridge moiety to the silane sites. A preferred process consists of two steps. In the first step a Grignard reagent of the (protected) bridge moiety is reacted with a hydrosilane H Si $(CH_3)_n$ $X_{3-n}$ where X is Cl or Br and n varies from 0 to 2. The derived hydrosilane, containing from 1 to 3 bridge moieties, is then reacted with peripheral vinyl or allyl groups of the carbosilane dendrimer in a hydrosilylation reaction catalyzed e.g. by platinum (this latter reaction gives high yields e.g. 99%).

The dendrimer-star polymer is a hybrid of this bridge-modified silane or dendrimer and selected types of star-forming polymer arms. These outer polymer arms may be formed either by:

(i) polymerizing selected monomer in situ with the silane or dendrimer serving as initiator, or by (ii) attaching selected preformed polymer chains at the reactive group sites. Preferably the polymer arms have terminal modifiable functional groups selected from hydroxyl, aldehyde or keto, amino, carboxyl and thiol. These terminal groups may have protecting groups as outlined above.

In the case of polymerization in situ of the polymer arms suitable monomers are:

a) for polyether arm: alkylene oxide, alkylene glycol, the alkylene have 2–4 C atoms;

b) for polysulfide arm: alkylene sulfide, alkylene dithiol (analogous to the polyether); and c) for polyester arm: glycolic acid lactone (glycolide), lactic acid lactone occurring in L-, D-, DL-forms and racemic mixtures (lactide) and -caprolactone.

These monomers may be used alone, consecutively, or as mixtures. Copolymers (including block copolymers) of these types of monomers can be used as arms.

The polymerization of the alkylene oxides is carried out in general by anionic polymerization.

The bridge reactive groups for the alkylene oxide or glycol type monomers are selected to be hydroxyl and transformed into alkoxide initiator sites by alkali metal (preferably K). In the case of the glycol-type monomer, the polymerization may be carried out by mineral acid catalysis. These polyether chains will have terminal hydroxyl or alkoxide groups.

For polymerization of the thio monomers, similar conditions as for the alkoxide and glycol type monomers may be used. These polysulfide chains will have terminal thiol or alkali metal (thiol) groups. Suitable initiator sites on the bridge for the thio monomers are the thiols and their alkali metal salts.

The polymerization of the lactone-type monomers is carried out, in general, by coordination polymerization. Typical catalysts are tin octoate and trialkyl aluminum. For this type the initiator site usually is the hydroxyl group. These polyester chains typically will have terminal hydroxyl groups formed from alkoxide groups by acid treatment.

The in situ polymerizations preferably are of the ring-opening type in which monomers polymerize end-to-end and form straight chains with minimal or no branching or cross-linking. This is desirable in this star polymer context because soluble polymers are obtained of controlled architecture and molecular weight. This type of straight chain is desired in the preformed polymer arms as well.

In the case of preformed chains, the polymerizations may be conducted in any suitable manner yielding a substantially straight chain with a reactive group at one end (which will serve or can be activated to serve, to attach the chain to the bridge reactive groups) and preferably a functional group at the other end. These polymerizations usually are selected from the following types: anionic (living) and coordination.

Attachment to the bridge may be carried out by any of the following procedures inter alia. Examples for each type of arm are summarized as follows:

a) Preformed polyether and preformed polysulfide: Williamson ether formation;

b) Preformed polyester: ester formation activated by dicyclohexylcarbodiimide.

Copolymers of any of these types can be preformed and used as arms.

We have found the in situ polymerization route to form the arms preferred over the preformed polymer attachment because of the reduced number of reaction steps, the larger molecular weight range obtainable, and the large number of arms that can be grown from a single core dendrimer. The resulting polymers(in situ type) are essentially free of contamination whereas the preformed route usually requires purification steps to recover the product.

Preferably the polymer arms have modifiable functional groups which can be modified to attach e.g. entities of the following types: bioactive agents including polypeptides, drugs and prodrugs, affinity ligands, polymerizable groups (e.g. (meth)acryl, styryl) and oligosaccharides.

Most suitably these functional groups are selected from hydroxyl, thiol, amine, carboxyl, halide and aldehyde with optional protecting groups therefor. Depending on the group present, it can be modified to form inter alia various ethers, sulfides, amides, esters and salts. The optional protective groups may be chosen from those mentioned previously.

The molecular weight of the polymer arms may range from about 500 up to about 100,000 or more, depending on the amount of monomer used, relative to the number of initiator sites present. For these polymer arms water solubility will tend to increase with increasing molecular weight, and within limits, this can be used to control the solubility of the star polymer. For many bio applications arm molecular weights within about 2000 to about 20,000 will be most suitable (assuming a core size of up to $G_3$ or $G_4$).

Controlling water solubility is important for applications such as drug carriers and conjugates with protein. The following variables affect the water solubility: dendrimer generation (G), type and length of the bridge, type and length of the polymer arm and nature of terminal groups. Selecting and adjusting one or more of these variables enables good control over solubility, especially water solubility.

The polyester star-dendrimer hybrids are advantageous for their low water solubility, biocompatibility, for their drug carrying properties and their propensity to slow degradation when in contact with biological fluids.

The following examples are illustrative:

EXAMPLE 1
Preparation of

17

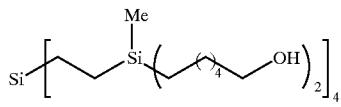

Magnesium turnings were introduced into a reaction flask and the flask purged with argon. A small iodine crystal was added and the mixture was stirred vigorously with occasional heating for fifteen minutes. The reaction flask was kept under vacuum until the purple iodine vapors disappeared. The flask was brought again under a slight pressure of argon and a THF (tetrahydrofuran) solution of 2-(6-chlorohexyloxy)tetrahydropyran 10 was added via cannula over the magnesium. The solution was degassed and then warmed to 55° C. when 1,2-dibromoethane was injected in portions over four hours. The generation of the organomagnesium was allowed to proceed overnight at the same temperature. The brown solution was cooled to 0° C. and treated dropwise with methyldichlorosilane and allowed to warm to room temperature and stirred for another four hours. After precipitation of magnesium chloride the flask was cooled to −10° C., quenched with methanol and poured over an iced 1M solution of HCl in water. After extraction with hexanes and concentration under vacuum, the crude product was purified by column chromatography on silica gel (5-15/95-85 v/v ether/hexanes) to give the hydrosilane (Bis-(6-(2-tetrahydropyranyloxyhexyl))-methylhydrosilane (15) in quantitative yield.

A hexane solution of 15 was dried by stirring over calcium hydride for 4 hours and filtered. Tetravinylsilane was added to this solution and then platinum catalyst was injected. The solution turned light yellow and warmed slightly, and was concentrated after one hour to an oily crude product. Purification by column chromatography afforded the desired reaction product G1-8THP.8-Cascade:silane[4](3-methyl-3-silapropylidyne)[1]:2-hexyloxy-tetrahydropyran (16) in 86% yield.

This G1-8[THP] 16 was dissolved in methanol and treated with a catalytic amount of para-toluenesulfonic acid. The deprotection was complete after 4 days at room temperature. The resulting methanolic solution was treated with sodium bicarbonate for thirty minutes then filtered. Basic alumina was added to the filtrate and the suspension was concentrated under vacuum. The resulting alumina dust was loaded on a chromatography column (dry loading technique). Purification by column chromatography on basic alumina (10/100 v/v ether/methanol and then pure methanol) provided the target polyol G1-8[OH]; 8-Cascade: silane[4]:(1-methyl-1-silapropylidyne)[1]:hexanol (17) in 97% yield.

This product was a 5 Si atom dendrimer with the 4 peripheral Si atoms each having attached (via a Si—C bond) two alkyl (6 C atom) bridges with a terminal hydroxyl group.

EXAMPLE 2
Preparation of

20

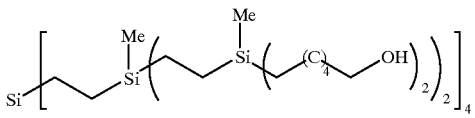

A hexane solution of bis-(6-(2-tetrahydropyranyloxyhexyl))-methylhydrosilane (15) was dried and filtered. The octavinylsilane

18

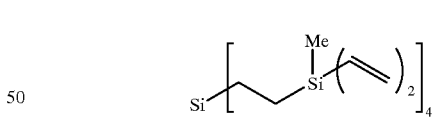

was added to this solution and then platinum catalyst was injected in one portion. The solution turned light yellow and slightly warmed up. The color became darker and the solution was concentrated after one hour to an oily crude product. Purification by column chromatography (40/60 v/v ether/hexane) afforded the reaction product G2-16[THP]; 16-Cascade:silane[4]: (1-methyl-1-silapropylidyne)[2]:2-hexyloxytetrahydropyran (19) in 86% yield.

This product G2-16THP 19 was dissolved in methanol and treated with a catalytic amount of para-toluenesulfonic acid. The deprotection was complete after 4 days at room temperature. The methanolic solution was treated with sodium bicarbonate for thirty minutes, then filtered through a plug of basic alumina. Concentration of the methanolic solution gave the target polyol G2-16 [OH].

16-Cascade:silane[4]:(1-methyl-1-silapropylidyne)$^2$: hexanol (20) in quantitative yield.

This dendrimer of generation 2 had a carbosilane of 13 Si atoms with the 8 peripheral Si atoms each having attached two alkyl bridges (6 C atoms) with 16 terminal hydroxyl groups.

EXAMPLE 3

Preparation of

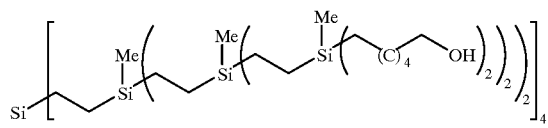

23

A hexane solution of bis-6-(2-tetrahydropyranyloxyhexyl))-methylhydrosilane 15 was dried and filtered. The filtrate was added over the corresponding hexadecavinylsilane 21

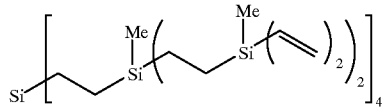

21 and treated with platinum catalyst until the solution turned light yellow and slightly warmed up. The color became darker and the solution was concentrated after one hour to an oily crude product. Purification by column chromatography (55/45 v/v ether/hexane) afforded the reaction product

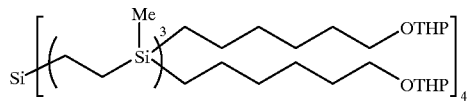

22 in 92% yield. The superscript 3 in formula 22 indicates the 3 generational layers involved.

This product G3-32[THP] 22 was dissolved in methanol and treated with a catalytic amount of para-toluenesulphonic acid. The deprotection was allowed to proceed for three days at room temperature and one more day at 40° C. The methanolic solution was treated with sodium bicarbonate for thirty minutes, concentrated and filtered through a plug of basic alumina. The filtrate was concentrated for one day under high vacuum to give polyol G3-32[OH]. 32-Cascade:silane[4]:(1-methyl-1-silapropylidyne)$^3$: hexanol(23) in 94% yield.

This generation 3 (G3) carbosilane had hexanol bridges bound (Si—C bond) to the peripheral Si atoms giving 32 terminal hydroxyl groups.

In another aspect, a core disilane can be used to prepare the carbosilane dendrimer in which case generation one (G1) will have 6 Si atoms, G2 12 Si, G3 24 Si and G4 48 Si atoms. Other variations are possible when other functionalities are desirable.

EXAMPLE 4

Synthesis of a 32-arm star polymer from the bridge-containing carbosilane core of Example 3 by in situ polymerization of ethylene oxide may be shown as:

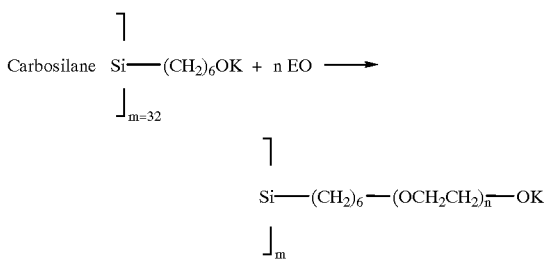

This procedure was carried out as follows. Reactants and reagents were purified and dried and the reaction vessel pumped and dried under vacuum. The solvent tetrahydrofuran THF was purified and distilled into the vessel. The modified carbosilane core (initiator) 23 from Example 3, potassium naphthalene, and cryptate, kryptofix™ (2,2,2) were added to the reaction vessel in that order (the cryptate aids solubilization and the polymerization reaction.). Next purified ethylene oxide was distilled into the vessel between −30° C. and 0° C. The reaction mixture was warmed to about 25° C. with stirring: after several hours the solution became clear. The polymerization was then completed in a second stage at about 40° C. The reaction was terminated with acetic acid and the star polymer precipitated in hexane and dried. Similar in situ polymerizations were carried out for the 16-arm polyethylene oxide (PEO), 8-arm and 4-arm PEO star polymers. Molecular weight distributions and intrinsic viscosities of these PEO arm star polymers are summarized in Table 1. The designations in the left column are sample numbers.

TABLE 1

Characteristics of Star Polymers With PEO Arms

| | $Mw \times 10^{-4}$ | $\frac{Mw}{Mn}$ | [η] (mL/g) | (Water 35° C.) |
|---|---|---|---|---|
| 4-arm star PEO | | | | |
| PEO15 | 0.61 | 1.07 | | |
| PEO14 | 2.19 | 1.06 | | 21.4 |
| PEO16 | 10.5 | 1.07 | | 73.2 |
| PEO17B1 | 17.8 | 1.06 | | 106 |
| PEO18B2 | 32.8 | 1.09 | | 165 |
| 8-arm star PEO | | | | |
| BC8PEO2K | 2.04 | 1.08 | | 12.0 |
| BC8PEO8K | 8.5 | 1.07 | | 35.4 |
| BC8PEO25kB1 | 15.0 | 1.06 | | 56.2 |
| BC8PEO60kB4 | 45.7 | 1.08 | | 133 |
| 16-arm star PEO | | | | |
| BC16PEO2kF1 | 4.8 | 1.06 | | 13.1 |
| BC16PEO6k | 14.2 | 1.07 | | 31.7 |
| BC16PEO5k | 19.2 | 1.09 | | 39.0 |
| BC16PEO16k | 32.6 | 1.07 | | 58.6 |
| 32-arm star PEO | | | | |
| BC32PEO4kB3 | 19.4 | 1.08 | | 22.9 |
| BC32PEO12kB2 | 38.1 | 1.09 | | 37.5 |

The molecular weights are given as g/mol. as determined by light scattering. Mn is number average molecular weight, Mw is the weight average molecular weight. The molecular weight distributions were determined by size exclusion chromatograpy. Intrinsic viscosities [η] in water are given as mL/g as determined by capillary viscosimetry. The polymers had narrow molecular weight distributions as evidenced by their Size Exclusion Chromatography traces in THF and in water. Solution properties of the star polymers have been studied and results indicated that the most desirable behaviours in solution were obtained at arm MW above about 2000.

Similar studies indicated that for uses such as bioconjugation the number of arms should be at least about 8 (i.e. core size at least about G1).

EXAMPLE 5
Star with Poly(L,L-lactide) Arms

The hydroxy-functionalized dendrimer 20 of Example 1 and tin octoate (1:20 with regard to hydroxy groups) were dried under high vacuum in a reaction flask. 5 gram of L,L-lactide held on calcium hydride at 100° C. for 30 minutes was then distilled into the reaction flask followed by 25 mL of dry toluene. The reaction flask was sealed under vacuum and polymerization carried out at 110° C. for 24 hours. The polymer solution was allowed to cool to room temperature, diluted with chloroform and polymer precipitated in methanol. Yield of star polymer was 80%. Size exclusion chromatography indicated a narrow molecular weight distribution, Mw/Mn=1.10–1.20. This polyester arm star polymer is useful as a biocompatible degradable polymer.

EXAMPLE 6
Functionalization of Star Poly(ethylene oxide)

3 gram of a 4-arm star poly(ethylene oxide) having a hexanol bridge silane core ($2.1 \times 10^{-3}$ mole OH groups) was treated with 0.104 g methacryloyl chloride ($1.0 \times 10^{-3}$ mole) in dry benzene in the presence of 0.146 mL triethylamine ($2.1 \times 10^{-3}$ mole) at room temperature overnight. The polymer was precipitated in n-hexane. NMR analysis indicated 26.7% OH substitution i.e. equivalent to one methacryl group per star polymer on average. 0.101 g of the end-functionalized poly(ethylene oxide) was copolymerized with 0.84 g methylmethacrylate in benzene at 55° C. in the presence of benzoylperoxide. Yield was 0.144 g (17%). Size exclusion chromatography showed a bimodal polymer formed of a high molecular weight broad distribution polymer, insoluble in methanol, and the original poly (ethylene oxide) star polymer. NMR analysis of the insoluble fraction indicated it contained 9% poly(ethylene oxide). This copolymer is useful for surface modification of polymethylmethacrylate to render the latter more biocompatible.

EXAMPLE 7
Functionalization of Poly(ethylene oxide).

This example indicates other types of groups that can be formed on star arms having terminal hydroxyl groups. A poly(ethylene oxide) solution in THF was treated with an equimolar amount (based on hydroxy groups) of sodium naphthalene and then treated with a mixture of p-chloromethylstyrene and ethylbromoacetate. $^1$H NMR indicated the statistical incorporation of both styrenic double bonds and acetate ester groups. The double bonds are useful in copolymerization of star poly(ethylene oxide) with other monomers. Such ester groups may be chosen for conversion to carboxylic acid. These examples are intended to be illustrative only and should not be considered limiting or exhaustive in any sense.

What is claimed is:

1. A silane- or carbosilane-based, periphery-modified dendrimer, adapted to serve as core in hybrid dendrimer-star polymers, comprising:
   a) an inner structure having a central silane nucleus and, optionally, multiple carbosilane branches extending outwardly from the nucleus in a repetitive generational manner yielding silane termini;
   and, attached to the silane or silane termini by a hydrolysis-resistant bond;
   b) bridge moieties comprising groups selected from alkyl of at least 4C atoms, cycloalkyl, aryl including aralkyl and alkaryl, and polyether and polysulfide of up to about 6 repeating units, the moieties having reactive groups enabling attachment of polymer arms thereto.

2. The dendrimer of claim 1 wherein the bridge b) comprises one of:
   (1)—R—X; where R is selected from alkyl and cycloalkyl having from 4 to 18 C atoms; aryl, aralkyl and alkaryl having form 6 to 18C atoms; and X is hydroxyl, thiol, amine, carboxyl, aldehyde, halide or a protecting group therefor;
   and
   (2)
   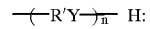
   where R' is alkyl having from 2 to 4C atoms, Y is oxygen or sulfur and n is 2 to 6, and the hydrolysis-resistant bond being Si—C.

3. The dendrimer of claim 2 wherein the bridge b) is selected from ($C_4$ to $C_{12}$ alkyl)—Z, (cyclohexyl, phenyl or benzyl) —Z, and
   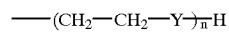
   where Z is —OH, —SH, —NH$_2$ or —COOH; Y is —O— or —S— and n is 2 to 6.

4. The dendrimer of claim 1 wherein each bridge moiety b) has one or two reactive groups, enabling attachment of one or two arms.

5. A hybrid dendrimer-star polymer, comprising:
   (i) a silane-or carbosilane-based, periphery-modified dendrimer, comprising:
      a) an inner structure having a central silane nucleus and, optionally, multiple carbosilane branches extending outwardly from the nucleus in a repetitive generational manner yielding silane termini;
      and, attached to the silane or silane termini by a hydrolysis-resistant bond;
      b) bridge moieties comprising groups selected from alkyl of at least two C atoms, cycloalkyl, aryl including aralkyl and alkaryl, and polyether and polysulfide of up to about 6 repeating units, the moieties having reactive group sites; and
   (ii) outer arms comprising polymer chains selected from polyethers, polysulfides, polyesters and copolymers thereof, the arms being attached to the dendrimer at the reactive group sites.

6. The star polymer of claim 5 wherein said polymer arms have functional groups thereon.

7. The star polymer of claim 6 wherein said functional groups are selected from hydroxyl, aldehyde, thiol, amine, carboxyl, halide and protecting groups therefor.

8. The star polymer of claim 6 wherein said arms comprise one of polyalkylene ethers, the alkylene group having from 2 to 4C atoms, and polyalkylene esters, the alkylene group having from 2 to 6 C atoms, and said functional groups are hydroxyl.

9. The star polymer of claim 5 wherein the outer arm molecular weight and is selected within the range from about 500 to about 100,000 to give the desired water solubility.

10. The star polymer of claim 5 wherein the modified dendrimer has a carbosilane core of size from generation 1 to generation 5.

11. The star polymer of claim 6 wherein said functional groups have been reacted to introduce polymerizable groups of the vinylic type.

12. The star polymer of claim 7 wherein said functional groups have been reacted to attach various carboxylic acid moieties.

13. The star polymer of claim 8 wherein the arms are polyalkylene esters selected from polyglycolide, poly-L-lactide, poly-D-lactide, poly-D,L-lactide and racemic mixtures thereof, and poly-caprolactone.

14. A process of preparing a hybrid dendrimer-star polymer including a modified silane or carbosilane dendrimer and selected polymer outer arms, comprising:
  a) attaching bridge moieties to reactive silane sites in a silane or carbosilane dendrimer, the bridge comprising a group selected from alkyl, cycloalkyl, aryl, aralkyl, alkaryl, small polyether and small polysulfide, the bridges having reactive groups thereon; and
  b) reacting a selected form of the bridge reactive groups with one of:
    (i) monomer selected from alkylene oxide, alkylene sulfide, alkylene glycol, alkylene dithiol, and hydroxyalkanoic acid and lactone thereof, under polymerization conditions, said selected form serving as initiator, to form polymer arm attached to the bridge; and
    (ii) prepolymer selected from polyether, polysulfide, polyester, and copolymers thereof to attach prepolymer to the bridge, thereby to form the star polymer.

15. The process of claim 14, wherein functional groups are present or formed on the polymer arms and these groups are reacted to introduce polymerizable groups which are then copolymerized with other monomers.

16. The process of claim 14, wherein step b) (i) polymerization conditions are controlled to yield a narrow molecular weight distribution and the molecular weight selected by adjusting the ratio of monomer to bridge reactive groups.

17. The process of claim 14, wherein step a) attachment reaction is one of:
  (i) reaction of silicon chloride sites with Grignard type organometallic bridge reagent, and
  (ii) hydrosilylation of unsaturated carbosilane sites with hydridosilane containing from one to three of the protected bridge moieties.

18. The process of claim 14 step b) (i) wherein the bridge reactive group is hydroxyl activated by potassium and the monomer is an alkylene oxide.

19. The process of claim 18 wherein the polymerization is carried out in a first stage at about 25° C. and in a second stage at about 40° C.

20. In a star polymer having a silane or carbosilane core and outer arms comprising polymer selected from polyether, polysulfide, polyester and copolymers thereof, the improvement comprising selected bridge inserts positioned between the core and the arms, with the bridge attached to silicon atoms in the core by a Si—C bond, the length and type of the bridge and of the arm being selected to give desired properties to the star polymer.

* * * * *